United States Patent [19]

Duran

[11] Patent Number: 5,376,112
[45] Date of Patent: Dec. 27, 1994

[54] VALVELESS CONDUIT WITH SIGMOID VALVE ANNULOPLASTY RING

[76] Inventor: Carlos G. Duran, Wellington Court 116 Knightsbridge, London SW11, England

[21] Appl. No.: 34,223

[22] Filed: Mar. 19, 1993

Related U.S. Application Data

[62] Division of Ser. No. 825,913, Jan. 27, 1992, Pat. No. 5,258,021.

[51] Int. Cl.[5] ............................................. A61F 2/24
[52] U.S. Cl. ............................................. 623/2; 623/900
[58] Field of Search ............................... 623/2, 900

[56] References Cited

U.S. PATENT DOCUMENTS 3,983,581 10/1976 Angell et al. .
4,106,129 8/1978 Carpentier et al. .
4,343,048 8/1982 Ross et al. .
4,451,936 6/1984 Carpentier et al. .
4,680,031 7/1987 Alonso .

OTHER PUBLICATIONS

Clinical Experience with Supported Homograft Heart Valve for Mitral and Aortic Valve Replacement, S. Sugie, et al., *The Journal of Thoracic and Cardiovascular Surgery*, vol. 57, No. 4, Apr. 1969, pp. 455–463.

*Primary Examiner*—Randy C. Shay
*Attorney, Agent, or Firm*—Klein & Szekeres

[57] ABSTRACT

A sigmoid heart valve annuloplasty prosthetic ring is disclosed which has a biocompatible stent molded into a scalloped shape, having three sinusoidal struts, to adapt to the anatomical shape of the annulus of the human sigmoid valves. The prosthetic ring is covered with biocompatible cloth. The prosthetic ring can be incorporated into the extremity of a biocompatible tubular cloth which serves as a vascular prosthesis in order to permit the total replacement of the ascending aorta or pulmonary artery without replacing the sigmoid valve.

5 Claims, 7 Drawing Sheets

THE ANNULOPLASTY RING REDUCES THE DISEASED AORTIC CIRCUMFERENCE

AORTIC REGURGITATION

FIG.6A

COMPETENT VALVE

FIG.6B

THE ANNULOPLASTY RING DOES NOT INTERFERE WITH LEAFLET MOVEMENT

DIASTOLE

FIG.7A

SYSTOLE

FIG.7B

DIFFERENCE BETWEEN ANNULOPLASTY RING (FIG. 8A) AND BIOPROSTHESIS STENT (FIG. 8B).

DIFFERENT PURPOSE (VALVE CONSERVATION VS REPLACEMENT)
DIFFERENT DESIGN
DIFFERENT CONSTRUCTION
DIFFERENT SURGICAL TECHNIQUE

VALVELESS CONDUIT WITH SIGMOID VALVE ANNULOPLASTY RING

CROSS-REFERENCE TO RELATED APPLICATION

The present application is a divisional of U.S. application Ser. No. 07/825,913, filed on Jan. 27, 1992, issued as U.S. Pat. No. 5,258,021.

1. Field of the Invention

The present invention is in the field of heart valve implantations. More particularly, the present invention is directed to the permanent implantation of a prosthetic ring in the annulus of human sigmoid valves (aortic or pulmonary) to remodel them so as to make the valve competent and avoid its replacement with an artificial heart valve. The present invention is also within the surgical field of heart valve reconstruction or repair.

3. Brief Description of the Prior Art

Heart valves are deformed by a variety of pathological processes. The vast majority of the patients have their valves replaced by artificial valves which are of two main types: 1) The "mechanical" valves, made of metal or plastic material, and 2) The "tissue" valves made from animal tissue. These tissue valves use bovine pericardium or a porcine aortic valve which is chemically treated and supported by suturing it to a stent or frame that simplifies its insertion into the annulus of the patient after excision of the diseased aortic or pulmonary valve. These have been termed "bioprosthesis". Several stents for the support of tissue valves have been described and/or patented:

Sugie et. al. (J Thorac Cardiovasc Surg 57:455, 1969. "Clinical experience with supported homograft heart valve for mitral and aortic replacement") describes a support stent that has a circular base with three vertical single posts. The stent is cloth covered so that a tissue aortic valve can be sutured on its inner aspect. The stent cannot be placed at the level of the aortic valve of a patient without previously excising it. Its flat base in a single plane cannot adapt to the curvatures of the patient's own leaflet insertions and therefore cannot be introduced inside the aortic valve. It is designed for mounting a tissue valve in its interior.

W. W. Angell, U.S. Pat. No. 3,983,581, describes a "stent for a tanned expanded natural tissue valve". The stent comprises a frame whose interior configuration is the anatomical negative of the exterior configuration of a tanned expanded aortic tissue valve. The described device can only be placed on the exterior of an aortic valve and not inside because it would interfere completely with the normal movements of the three leaflets.

A Carpentier and E. Lane, U.S. Pat. No. 4,451,936, describe "an aortic prosthetic valve for supra-annular implantation comprising a valve body of generally annular configuration and a valve element movable". "The valve body terminates in a generally annular base and a scalloped suture ring . . . which fit the contour of the sinuses of valsalva at the base of the aorta". This device, although it conforms better to the anatomy of the aortic annulus, cannot be placed inside the aortic root without excising the patient's own aortic valve. Its suturing base requires excision of the three leaflets. It is not designed to be used as an annuloplasty device but as a valve replacement.

D. N. Ross and W. J. Hoskin, U.S. Pat. No. 4,343,048 describe a stent for holding in its interior a tissue valve "for the replacement of defective cardiac valves". "The non viable valve is mounted within". The stent design is such that it cannot be placed within the aortic root without excising the patient's native valve. A feature described to be important in this patent is the flexibility of the stent in order to reduce the stress on the mounted tissue valve.

A. Carpentier and E. Lane, U.S. Pat. No. 4,106,129, describe a new bioprosthetic heart valve that is supported by a wire frame with U shaped commissural support. This support frame supports a preserved porcine xenograft or xenografts from other species, or an allograft (homograft). This patent does not mention using this support frame for remodelling the diseased annulus of a native aortic valve, nor is this structure adapted for such remodelling. This follows, when the general shape of the wire frame shown and described in this patent is considered. The commissure supports are parallel, the base is flat and the inflow and outflow orifices are similar. This structure is obviously designed for supporting a tissue valve but not for being implanted inside an aortic root without previously removing the three native leaflets.

All artificial or prosthetic heart valves, whether mechanical or bioprosthesis, although greatly improving the condition of the patient, have some serious drawbacks, namely: thrombogenicity (tendency towards thrombus formation and subsequent detachment with embolization) and limited durability secondary to mechanical or tissue structural failure.

Other complications such as noise, hemolysis (destruction of blood elements), risk of endocarditis (valve infection) and partical dehiscence of the valve also occur. Because of the risk of embolism, the majority of patients who receive artificial heart valves need to take anticoagulative medication for life with the concomitant risk of hemorrhage and necessary change in life style.

Different and more recent developments in the field of cardiac surgery included attempts to surgically repair diseased heart valves. A variety of surgical maneuvers or procedures have been used for this purpose. This type of reconstructive heart valve surgery has been shown to be far superior to valve replacement. References to such reconstructive heart valve surgery can be found, for example, in the following articles: Angell WW, Oury JH, Shah P: A comparison of replacement and reconstruction in patients with mitral regurgitation. J Thorac Cardiovasc Surg 93:665, 1987; and Lawrence H. Cohn, M.C., Wendy Kowalker, Satinder Bhatia, M.D., Verdi J. DiSesa, M.D., Martin St. John-Sutton, M.D., Richard J. Shemin, M.D., and John J. Collins, Jr., M.D.: Comparative Morbidity of Mitral Valve. Repair versus Replacement for Mitral Regurgitation with and without Coronary Artery Disease. Ann Thorac Surg 45:284-290, 1988.

Reconstructive surgery, however, is difficult to perform and is not always possible in every patient. Among the variety of reconstructive maneuvers, valve annuloplasty is the most frequently performed in the tricuspid and mitral valves. Valve annuloplasty is an operation which selectively reduces the size of the valve annulus. For this purpose, a number of prosthetic rings have been developed for the atrioventricular valves and are used in an increasing number of patients all over the world. The best known commercially available rings are the Carpentier (distributed by Edwards Labs) and the Duran (distributed by Medtronic Inc.) rings. These are described in the following references: Carpentier A, Chauvaud S, Fabiani JN, et. al.: Reconstructive surgery of mitral incompetence: ten year appraisal. J Thorac Cardiovasc Surg 79:338, 1980; Duran CG, Ubago JL: Clinical and hemodynamic performance of a totally flexible prosthetic ring for atrioventricular valve reconstruction. Ann Thorac Surg 22:458–63, 1976; and Duran CG, Pomar JL, Revuelta JM, et. al.: Conservative operation for mitral insufficiency: critical analysis supported by postoperative hemodynamic studies in 72 patients. J Thorac Cardiovasc Surg 79:326, 1980.

The Carpentier and Duran rings, however, can only be used in the mitral and tricuspid valves. It is surprising that although many stents for supporting aortic tissue valves (bioprosthesis) have been described and patented (vide Supra) none has been even suggested as a possible aortic annuloplasty ring. In fact their design make it impossible to be used for this purpose. According to the best knowledge of the present inventor, to date there has been no description nor use of a prosthetic ring for annuloplasty of sigmoid valves (aortic or pulmonary).

Furthermore, an important number of patients develop a pathological dilatation (aneurysm) of the ascending aorta which requires its replacement, particularly when a tear occurs (dissection). This dilatation of the aorta also involves the aortic valve annulus, giving rise to an insufficiency due to lack of coaptation of the valve leaflets, which are otherwise normal. The prior art solution to this problem has been the replacement of the ascending aorta with an implanted artificial "valved conduit". Such a "valved conduit" comprises a biocompatible cloth tube provided with an artificial (mechanical or tissue) valve. Mere replacement of the aorta with a "valveless" artificial conduit while leaving the natural valve in place, is not generally recommended in the art, due to the dilated nature of the valve annulus and due to the danger of further dilation of the unsupported annulus. However, it is also generally recognized in the art that implantation of "valved conduits" raises risks at least of the same complications as other valve replacements.

In view of the foregoing, and to avoid the above noted disadvantages, there is a genuine need in the prior art for a better approach to the treatment of aortic or pulmonary insufficiency. The present invention provides such a better approach.

SUMMARY OF THE INVENTION

The basic and general object of the present invention is to provide a structure that maintains the aortic or pulmonary sigmoid valves in normal shape, or induces such valves to regain their normal shape.

More specifically, when performing a sigmoid valve annuloplasty, the object of the present invention is to implant a device which reduces, to the desired size, the circumference of the diseased aortic or pulmonary valve. This is achieved by the permanent implantation of a prosthetic ring which has the shape of the annulus of the sigmoid valves (aortic or pulmonary) and which, when properly sized, reduces the sigmoid valve circumference, making possible contact of the native valve leaflets. Thus, as a result of the implantation, the native valve becomes competent again.

The invention comprises a stent, circular in shape from above and below, but scalloped so as to follow the contours of each of the three sinuses of the natural heart valve. These sinuses are sometimes referred to in the anatomical art as "sinuses of Valsalva". The stent therefore has three curved "sinusoidal" struts and three round bases, all in continuity.

The stent which in one preferred embodiment comprises biocompatible solid metal single wire, plastic or reabsorbable polymer structure, has a wider diameter at its base than at its upper end, assuming in this respect, the general configuration of a truncated cone. The height of the three "sinusoidal" struts and the distance between their ascending and descending limbs varies with the diameter of the ring. To fit various patients a number of different size rings are required, their base or inflow orifice diameters ranging from 15 to 35 mm.

For implantation the stent is covered with biocompatible cloth. The use of such cloth or fabric mesh to enclose various plastic and/or metal members which are subsequently surgically implanted in the human body is, per se, known in the art. This mesh or cloth, in accordance with standard practice in the art, is relatively thin, preferably it is approximately 0.3 mm thick.

In another preferred embodiment the ascending and descending sinusoidal struts of the described stent are solid but interrupted at the level of the upper and lower connecting curves. Continuity is established by the biocompatible strut covering cloth which stretches from one strut to the next one. In this fashion the general configuration of the stent is maintained. The lower (inflow) and upper (outflow) circumferences remain similar while a certain degree of mobility of each part of the stent is possible.

In order to use the stent in cases where not only the aortic valve is incompetent but also the ascending aorta is pathologically dilated, a valveless conduit is fashioned to be attached to the stent. For this purpose a cloth tube of the type already known in the art, made of biocompatible material which is used for vascular substitution, is formed at one of its ends in a scalloped fashion to follow the contours of the sinusoidal stent, and is sutured to the stent. In one embodiment, the tube has a substantially constant diameter. In another embodiment the tube is shaped so as to form between each strut of the stent a sinus or bulge. A sewing ring or skirt is incorporated at this extremity to permit the suturing, by the surgeon, of the "valveless conduit" to the patient.

The objects and features of the present invention are set forth in the appended claims. The present invention may be best understood, together with further objects and advantages, by reference to the following description, taken in connection with the accompanying drawings:

DESCRIPTION OF THE PREFERRED EMBODIMENTS

The following specification taken in conjunction with the drawings, sets forth the preferred embodiments of the present invention. The embodiments of the invention disclosed herein are the best modes contemplated by the inventor for carrying out his invention in a commercial environment although it should be understood that various modifications can be accomplished within the parameters-of the present invention.

Figure 1:
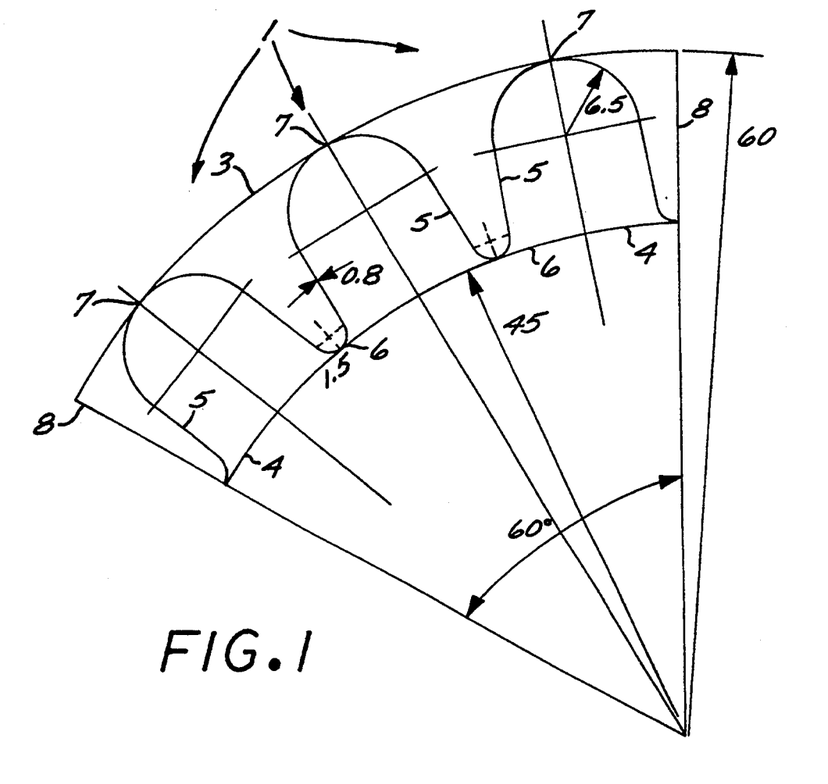
FIG. 1 is a lateral view of the preferred embodiment of the solid stent of the present invention, showing the stent as a flat pattern.
Figure 2:
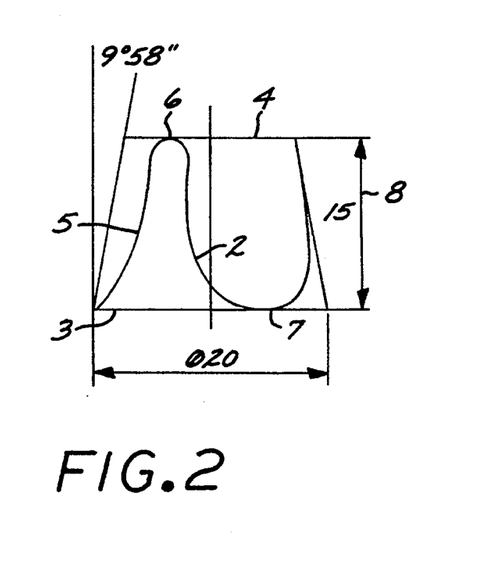
FIG. 2 is a lateral view of the preferred embodiment of the solid stent, showing the relationship of its height to diameter and the difference between the "inflow" and "outflow" diameters.
Figure 3:
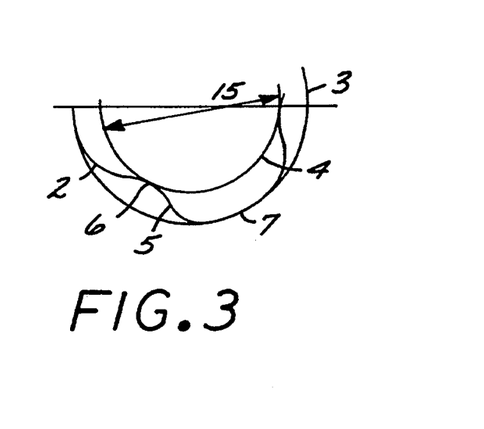
FIG. 3 is a top view of the preferred embodiment of the solid stent, showing again the difference between the inflow (outer) and outflow (inner) diameters.

Referring now to the drawing Figures, and particularly to FIGS. 1-3, the preferred embodiment of the sigmoid valve annuloplasty ring 1 of the present invention is disclosed. It should be noted at the outset that although the ensuing description is primarily directed to the use of the annuloplasty ring 1 in the aortic valve area, the invention is not so limited. Rather, the annuloplasty ring 1 can be also applied to the other sigmoid valve of the human (or animal) anatomy, namely to the pulmonary valve.

Referring now specifically to FIG. 1, an important feature of the present invention is the configuration or shape of the stent of the annuloplasty ring 1. Specifically, the oval stent 1 of the invention has a shape adapted to follow the contour of the normal sigmoid valve. The stent 1 in the first preferred embodiment is constructed from a single solid piece of biocompatible metal. A preferred metal for the stent is titanium or titanium alloy, normally used for implantation. This alloy has very good properties for the present purpose, as well as combining strength with lightness, it is biocompatible.

Biocompatible non-absorbable plastic materials can also be used for the stent, although they would probably need to be thicker than metal, in order to have sufficient strength. Another alternative is the use of biocompatible polymers that are reabsorbed by the organism after a certain time after their implantation.

The solid single piece 2 of the first preferred embodiment of the stent 1 is shaped into the herein described configuration, which is depicted in FIGS. 1, 2, 3 and 4.

The stent 1 has a circular appearance of configuration, when it is viewed from the top or bottom, as is shown on FIG. 3. The "circle" 3 on the bottom represents a wider "inflow" orifice, and the "circle" 4 on the top represent a smaller "outflow" orifice. Thus, as is shown in the drawing figures (principally FIGS. 1-4) the stent forms a "convoluted ring" having three substantially sinusoidal struts 5 which project upwardly from the base "diameter" of the convoluted ring. The ring itself is curved both at its lower (inflow) and upper (outflow) ends so that if placed on a horizontal plane it would only make contact in three points. Each strut has a separate descending and an ascending portion 5 which are generally nonparallel relative to one another. These ascending and descending limbs 5 are joined by smooth curved upper 6 and lower 7 portions (FIGS. 1, 2, 3, 4). These joining parts are curved both in the frontal or lateral and axial view (FIGS. 1, 2 and 3). The angle formed by the ascending and descending limbs 5 in relation to the vertical is substantially 10° (FIGS. 1 and 2).

Figure 4:
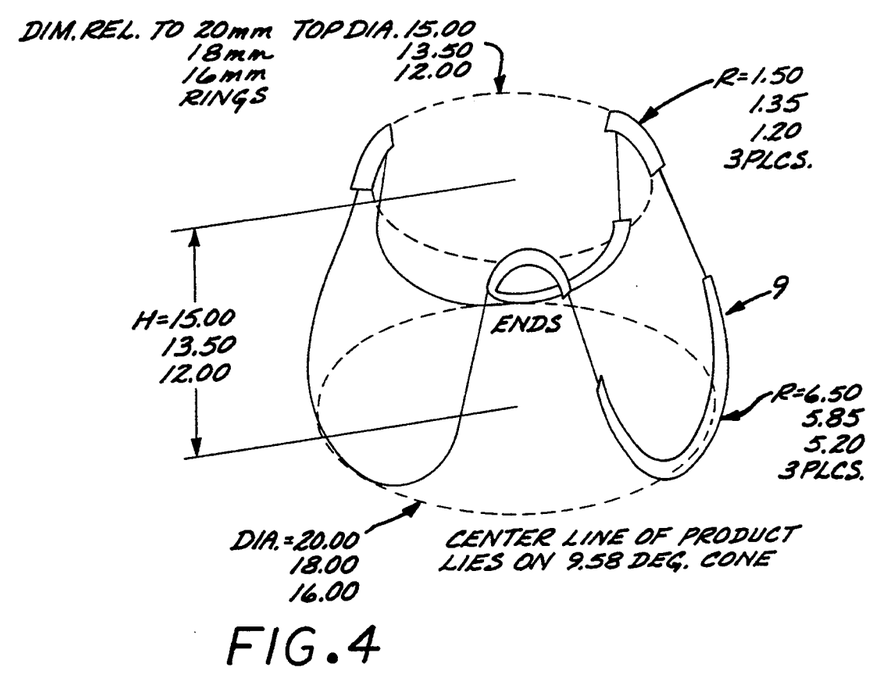
FIG. 4 is a perspective view of the preferred embodiment of the stent with the relative measurements of each of its parts in relation to the inflow diameter.

Proportions between the height and width of the stent can be varied, for as long as the stent meets its stated objective to reduce the circumference of a diseased annulus to its substantially normal size, and to permit the native valve leaflets to seal against each other as shown in FIG. 4. An exemplary-stent 1 depicted in the drawings has the following dimensions: the diameter of the lower "inflow" orifice circle 3 is 20 mm, the diameter of the upper "outflow" orifice circle 4 is 15 mm, the total height 8 of the stent 1 is 15 mm, and the radii of the "turns" of the stent 10 form the sinusoidal struts are 1.5 mm for the upper 6 and 6.5 mm for the lower 7 curve. Those skilled in the art will recognize that the foregoing dimensions and proportions can be varied within certain limits; nevertheless preferably the proportions described above and shown in the drawings are maintained. Limits of the dimensions are to be construed in this regard to be such, that the stent of the invention must approximate the natural shape of the normal heart valve. With respect to the actual "inflow" and "outflow" diameters of the stent 1 (as opposed to relative proportions), the stent 1 of the invention must be manufactured in different sizes to accommodate the different sizes of the human sigmoid valve, which itself varies for each individual. An approximate range of such sizes is between 15 to 35 mm for the inflow diameters. Dimensions of a number of examples of stents constructed in accordance with the invention to fit different patients, are given in FIG. 4.

For implantation the stent 1 is covered with biocompatible cloth. In this regard biocompatible cloth comprises a fabric mesh of biocompatible material, preferably polyester (polyacetate) fabric. The use of such biocompatible fabric mesh to enclose various plastic or metal members which are subsequently surgically implanted in the human body is well known in the art. As is further known, after implantation into the human body, an ingrowth of fibrous tissue usually forms in the interstitial spaces of the fabric, and endothelial cells cover the fabric to provide a nonthrombogenic autologous surface. Therefore, at least sometime after the implantation, the cloth covered metal or plastic member no longer causes coagulation of blood and presents no significant danger of thrombus formation when implanted in the heart.

Figure 5:
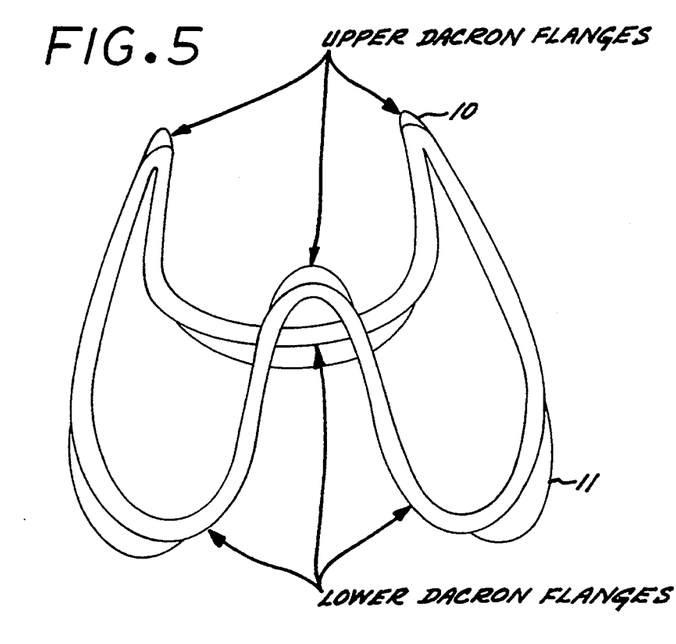
FIG. 5 is a perspective view of the preferred embodiment with the cloth covering showing the cloth flanges for holding the anchoring sutures.
Figure 6A:
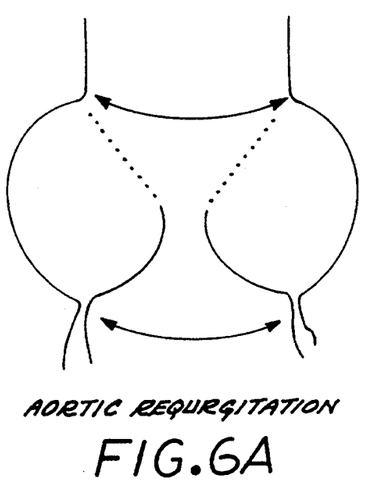
FIG. 6 is a schematic view of the patient's aortic valve before and after annuloplasty with the "Sigmoid Annuloplasty Ring".
Figure 6B:
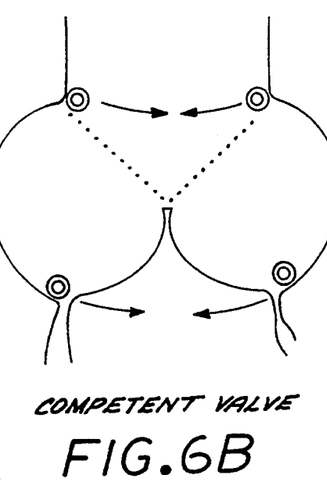
Figure 7A:
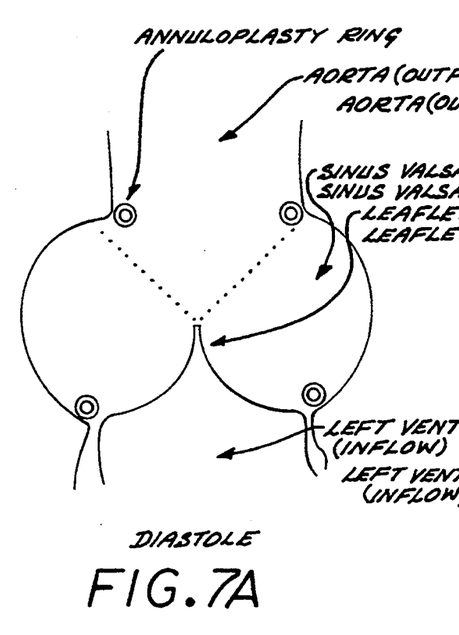
FIG. 7 is a schematic view of the patient's aortic root during systole and diastole after implantation of the "Sigmoid Annuloplasty Ring".
Figure 7B:
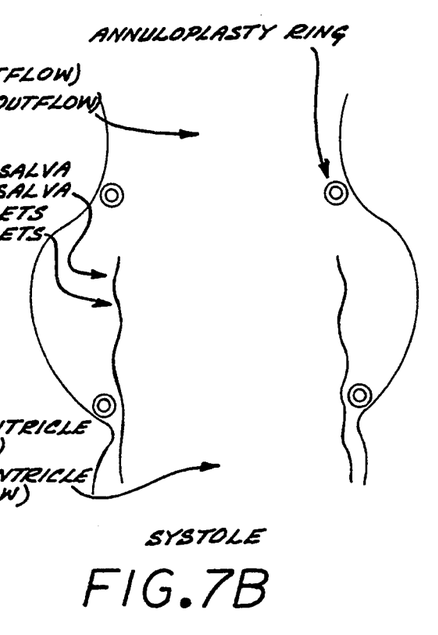
Figure 8A:
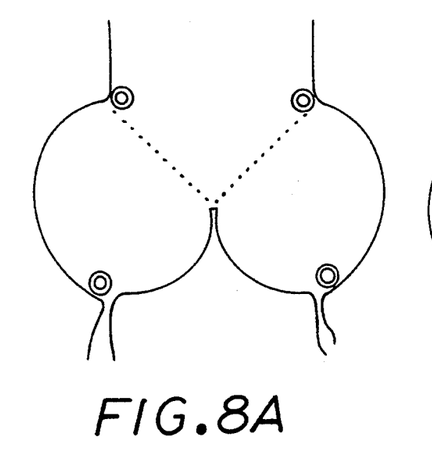
FIG. 8 is a schematic view of the patient's aortic root after ring annuloplasty (A) compared with after bioprosthesis replacement (B).
Figure 8B:
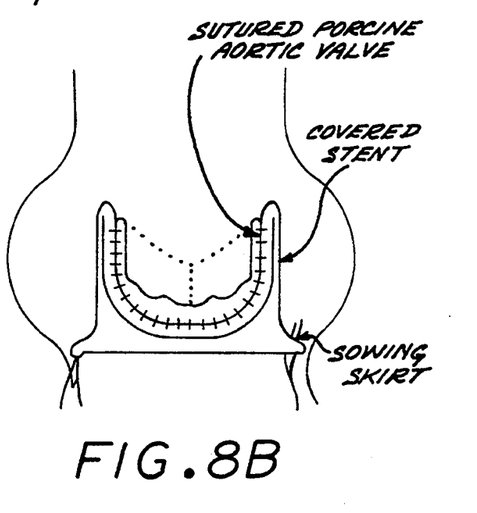
Figure 9:
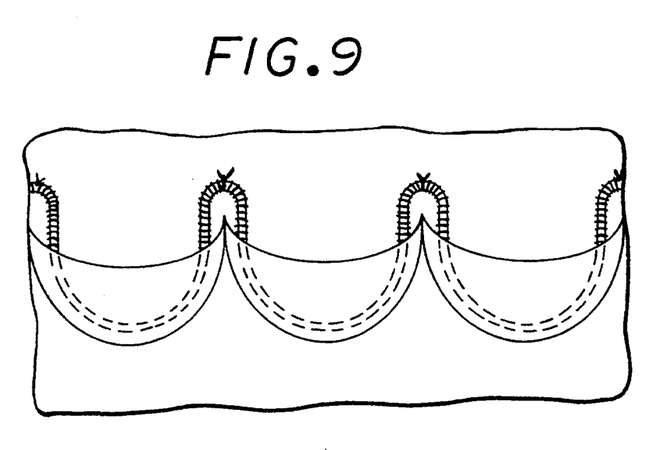
FIG. 9 is a schematic depiction of an opened sigmoid (aortic or pulmonary) valve (human or animal) showing the three native tissue leaflets and the annuloplasty ring (stent) of the present invention, placed inside the vessel without interference with the three normal leaflets and held to the arterial wall by a continuous suture.

In accordance with the present invention, the stent 1 is totally covered with this thin fabric, preferably of approximately 0.3 mm thickness, so that there are no plastic or metal surfaces exposed to come into contact with tissue or blood flow. The biocompatible cloth cover of the stent is best illustrated in FIGS. 4 and 5. Different modes of covering the stent are: (a) either by a single layer of cloth 9 in FIG. 4 that fits exactly the shape, thickness and dimensions of the stent, or (b) by doubling the cloth at the lowest and highest points of curvature of the sinusoids of the stent (10 and 11 in FIG. 5). The object of these flanges 10 and 11 is to simplify the identification by the surgeon of these points where the initial anchoring sutures must be placed. Six such sutures placed at the highest 10 and lowest 11 curvatures of the ring must coincide with a point above each commissure and at the lowest point of each sinus of Valsalva of the patient. It is important to avoid contact of the ring with any of the patient's own leaflets, as depicted in FIGS. 6 and 7 which show the mechanism of action of the present invention (FIG. 7) and how it does not interfere with the movements of the patient's sigmoid valve leaflets during the cardiac cycle (FIG. 8). Closure of the sigmoid valve returns to normal by leaflet apposition because of the reduction in the valve annulus induced by the ring. Thus, patients having an implant of the fabric covered stent 1 of the present invention may be gradually weaned from anti-thrombogenic medication, at least some time after the implantation. To emphasize, this is because, as soon as the cloth covered prosthesis (annuloplasty ring) is covered by human tissues, there are no exposed thrombogenic surfaces in the prosthesis and no further danger of embolus formation.

It is emphasized in connection with the annuioplasty ring or prosthesis of the invention, that it is not intended to serve as a heart valve prosthesis, nor as a stent for heart valve prosthesis. Rather, the present invention is an annuloplasty ring, a prosthesis which is to be implanted into the heart to function together with the native heart valve.

Figure 10:
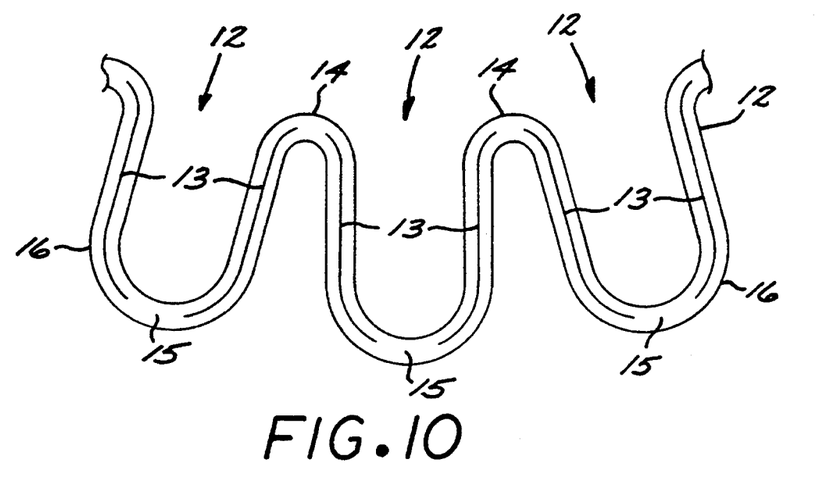
FIG. 10 is a lateral view of the second preferred embodiment of the stent of the present invention showing the stent in a flat pattern with the solid struts joined by the cloth cover.
Figure 11:
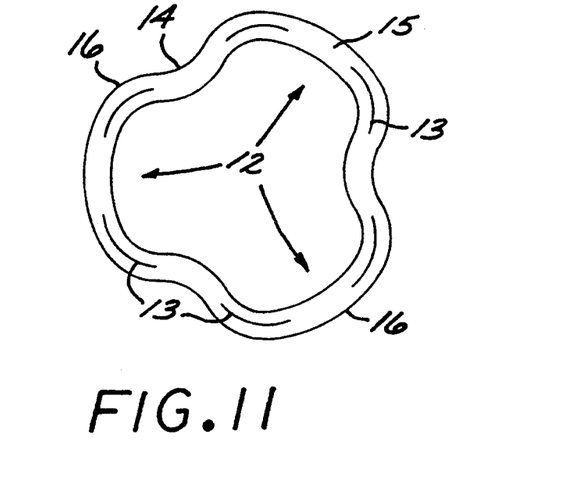
FIG. 11 is a top view of the second preferred embodiment of the stent showing the solid struts joined by the cloth cover.

The second preferred embodiment of the sigmoid ring 12 is depicted in FIGS. 10 and 11. In this preferred embodiment the struts 13 are made of solid material with the same configuration as in the first preferred embodiment (5 in FIGS. 1, 2, 3 and 4). However these struts 13 are interrupted at the level of the highest curvature 14 and lowest curvature 15 corresponding to 6 and 7 in the first preferred embodiment. Continuity of the stent 12 is re-established by the cloth covering 16 of the stent 12 which fits exactly over the ascending and descending solid limbs 13. In this second preferred embodiment there is no need for constructing cloth flanges for simplifying the suturing of the ring as shown at 10 and 11 in FIG. 5 of the first embodiment. In this second embodiment the anchoring sutures of the sigmoid annuloplasty ring can be passed without difficulty through the cloth at 14 and 15.

Figure 12:
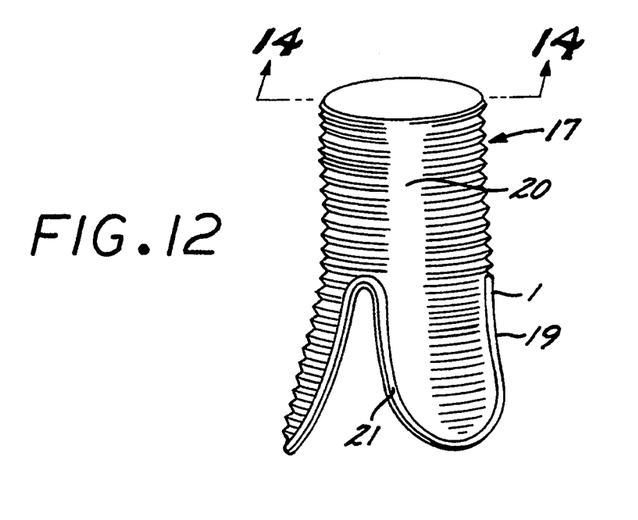
FIG. 12 is a perspective view of a first preferred embodiment of an aortic valveless conduit in accordance with the present invention, and incorporating the stent of the present invention.
Figure 13:
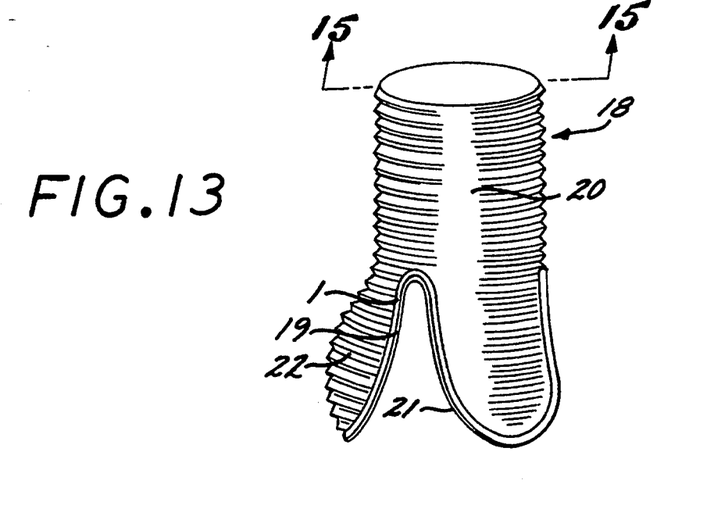
FIG. 13 is a perspective view of a second preferred embodiment of an aortic valveless conduit in accordance with the present invention, and incorporating the stent of the present invention and a vascular tube with sinuses of Valsalva.
Figure 14:
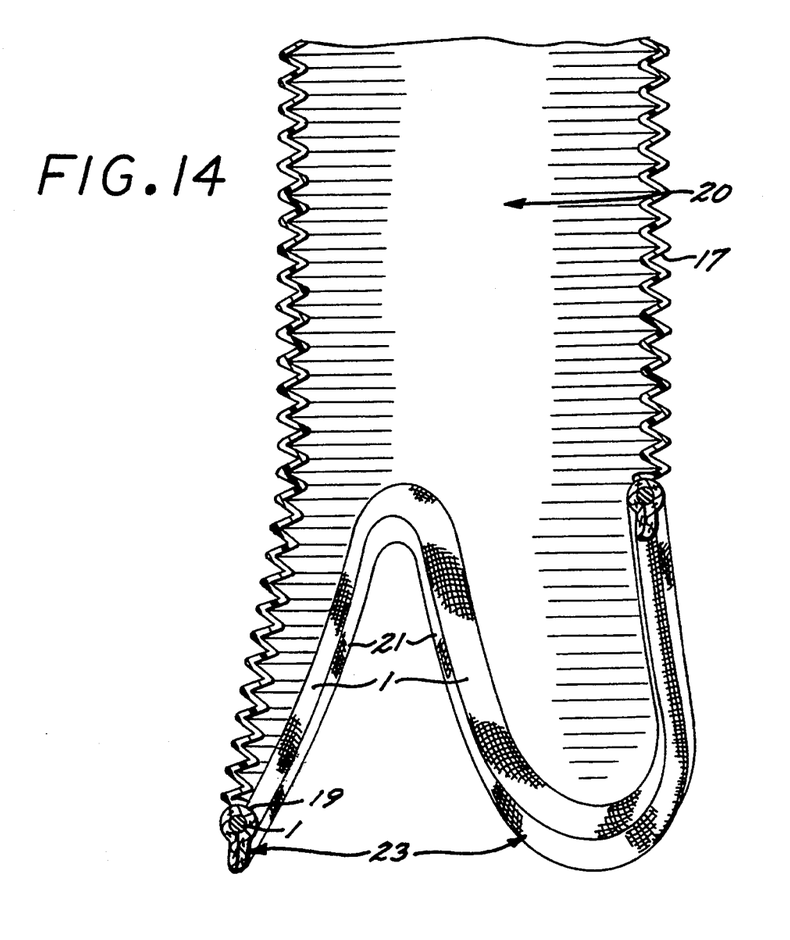
FIG. 14 is a cross-sectional view of the first preferred embodiment of the aortic valveless conduit, the cross-section being taken on lines 12A,12A of FIG. 12.
Figure 15:
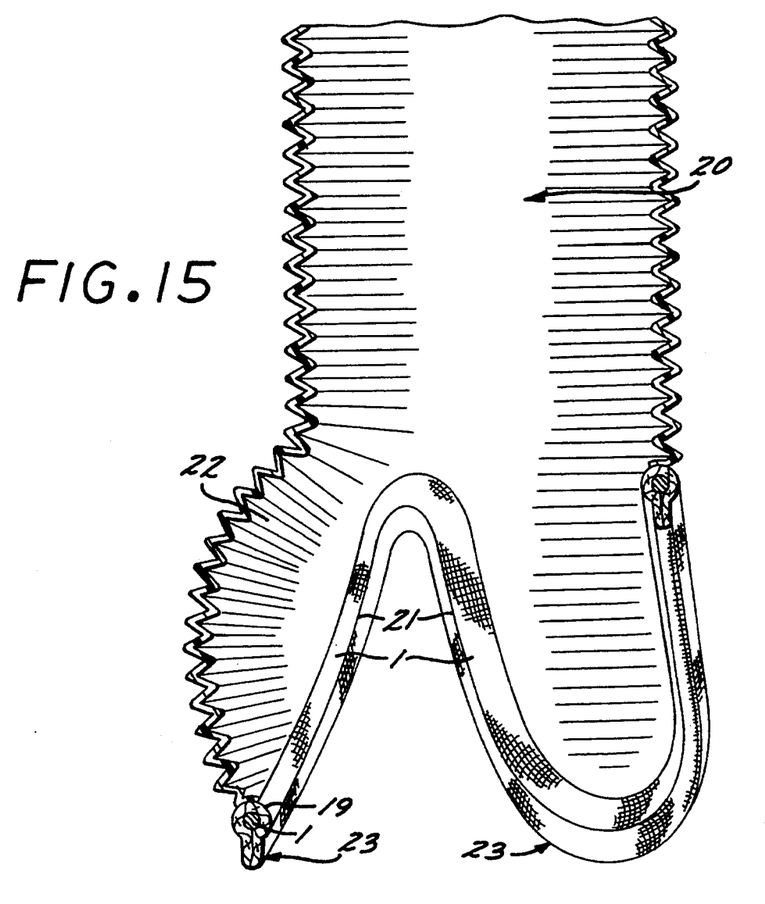
FIG. 15 is a cross-sectional view of the second preferred embodiments of the aortic valveless conduit, the cross-section being taken on lines 13B,13B of FIG. 13.

Referring now to FIGS. 12 and 13, a first embodiment and a second embodiment 18 of a valveless conduit are disclosed, each of which incorporates the novel annuloplasty ring or stent of the present invention. The valveless conduits are used when, in addition to remodelling of the aortic annulus, a portion of the ascending aorta must also be replaced because it is pathologically dilated.

As shown on FIGS. 12, 13, 14 and 15, the valveless conduit includes the stent 1 of the present invention, which is covered by biocompatible cloth or fabric 19. A cloth tube 20 of biocompatible material and of the type which is used in the state-of-the-art vascular substitutions is attached (by stitching or like means) to the stent 1. For this purpose, one end of the cloth tube 20 is formed (cut) in a scalloped fashion so as to conform to the configuration of the stent 1, and be attachable thereto. In accordance with the first preferred embodiment 17 of the valveless conduit, the cloth tube attached to the stent 1, as is shown on FIGS. 12 and 14, has a substantially constant diameter. In accordance with the second preferred embodiment 18 of the valveless conduit, the cloth tube 20 is configured to form between each strut 21 of the stent 1 a sinus or bulge 22 so as to duplicate the naturally occurring three sinuses of the heart valve (ginuses of Valsalva). A sewing ring or skirt 23 is also attached to the stent 1, or forms part of the cloth cover of the stent 1, to permit attachment by suturing of the valveless conduit to the remnants of the aortic wall of the patient. The sewing ring 23 requires no further detailed description here because it can be constructed in accordance with the state-of-the-art from the same materials which are used for sewing rings utilized in connection with mechanical and tissue heart valves.

Several modifications of the above described novel annuloplasty prosthesis and of the associated part and processes may become readily apparent to those skilled in the art in light of the above disclosure. Therefore, the scope of the present invention should be interpreted solely from the following claims, as such claims are read in light of the disclosure.

What is claimed is:

1. A valveless conduit comprising:
    a sigmoid heart valve annuloplasty prosthesis which includes a convoluted ring consisting essentially of material Selected from biocompatible plastics, metals, and reabsorbable polymers having the configuration which includes three substantially sinusoidally shaped struts projecting upwardly from a base diameter of the ring, the base diameter being larger than the diameter of the ring at the top of the sinusoidal struts, portions of the ring which form the base diameter and which interconnect the sinusoidal struts being curved both in a frontal and axial plane, the material forming each of the struts being generally non-parallel in separate ascending and descending portions of each strut, whereby in a side view the configuration of the ring approximates a truncated cone and whereby the overall configuration of the ring is such that native heart valve leaflets of humans or domestic animals may seal against each other within the sinusoidal struts of the ring;
    a biocompatible cloth covering substantially the entire ring;
    a biocompatible vascular tubular prosthesis comprising a biocompatible cloth tube which is configured at one end in a scalloped fashion to substantially match the configuration of the convoluted ring, the cloth tube being affixed to the convoluted ring at its scalloped end, and a sewing ring attached to the convoluted ring to permit suturing of the valveless conduit to tissues of the human or animal patient.

2. The valveless conduit of claim 1 wherein the biocompatible cloth tube comprises a bulge formed on each sinusoidal strut of the convoluted ring, thereby simulating the shape of natural sinuses of Valsalva.

3. The valveless conduit of claim 1 wherein the convoluted ring consists essentially of biocompatible plastic material.

4. The valveless conduit of claim 1 wherein the convoluted ring consists essentially of biocompatible metal.

5. The valveless conduit of claim 1 wherein the convoluted ring consists essentially of biocompatible reabsorbable polymer material.

* * * * *